US007669460B1

(12) United States Patent
Sandusky et al.

(10) Patent No.: US 7,669,460 B1
(45) Date of Patent: Mar. 2, 2010

(54) SMALL-SCALE SHOCK REACTIVITY AND INTERNAL BLAST TEST

(75) Inventors: Harold W. Sandusky, Fulton, MD (US); Richard H. Granholm, Bel Alton, MD (US); Douglas G. Bohl, Potsdam, NY (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 578 days.

(21) Appl. No.: 11/726,198

(22) Filed: Mar. 9, 2007

(51) Int. Cl.
*G01N 33/22* (2006.01)
(52) U.S. Cl. .................................. 73/35.16
(58) Field of Classification Search ............... 73/35.16, 73/35.14
See application file for complete search history.

(56) References Cited

U.S. PATENT DOCUMENTS

| | | | | |
|---|---|---|---|---|
| 4,474,052 A * | 10/1984 | Bodurtha et al. | ........... | 73/35.17 |
| 4,696,232 A | 9/1987 | Held | | |
| 6,173,662 B1 * | 1/2001 | Donovan | ..................... | 110/237 |
| 6,354,137 B1 * | 3/2002 | Guirguis et al. | ............ | 73/35.17 |
| 6,669,753 B1 | 12/2003 | Chambers et al. | | |
| 7,370,513 B2 * | 5/2008 | Meyer et al. | ................ | 73/35.15 |
| 2003/0209133 A1 * | 11/2003 | Greenfield et al. | ............. | 86/50 |

OTHER PUBLICATIONS

R.H. Granholm, H.W. Sandusky, Small-Scale Shock Reactivity and Internal Blast, Proceedings of 13th International Detonation Symposium, Aug. 2006.

R.H. Granholm, H.W. Sandusky, Small-Scale Shock Reactivity and Internal Blast, Shock Comp. of Cond. Matter-2005 (M.D. Furnish et al., Ed) AIP Conf. Proc. 845, 2006, 1257-1260.

H.W. Sandusky,R.H. Granholm, Prompt Reaction of Aluminum in Detonating Charges, Shock Comp. of Cond. Matter-2005 (M.D. Furnish et al., Ed) AIP Conf. Proc. 845, 2006, 1105-1108.

H.W. Sandusky, R. H. Granholm, and D.G. Bohl, Small-Scale Shock Reactivity Test (SSRT), IHTR 2701, Aug. 12, 2005.

H.W. Sandusky, R.H. Granholm, and D.G. Bohl, Small-Scale Shock Reactivity Test, in Proceedings of JANNAF 40th Combustion Subcommittee Meeting, JSC CD-39, Jun. 2005.

* cited by examiner

*Primary Examiner*—Hezron Williams
*Assistant Examiner*—Alex Devito
(74) *Attorney, Agent, or Firm*—Fredric J. Zimmerman

(57) ABSTRACT

An apparatus for conducting a small-scale shock reactivity and internal blast test (SSBT), and a related test method that simulates a large scale test of explosive materials while employing small quantities of materials for the characterization. The apparatus includes a small scale shock reactivity test (SSRT) device, and an internal blast test device including a pressure chamber with an accessible interior, a pressure transducer, a multipurpose port provides an electrical connection to the shock reactivity test device, and a small gas port. The SSRT device is housed within the pressure chamber, and gases and materials produced during a small scale shock reactivity test are quasi-statically retained by the pressure chamber. The pressure transducer is in communication with an instrument that can display the pressure detected in the pressure chamber for analysis.

3 Claims, 3 Drawing Sheets

SMALL-SCALE SHOCK REACTIVITY AND INTERNAL BLAST TEST

STATEMENT OF GOVERNMENT INTEREST

The invention described herein may be manufactured and used by or for the Government of the United States of America for Governmental purposes without the payment of any royalties thereon or therefore.

BACKGROUND OF THE INVENTION (1) Field of the Invention

The present invention relates generally to a test method for characterizing potentially explosive materials, and more particularly a test method that simulates a large scale test of explosive materials while only employing very small quantities of materials for the characterization.

(2) Description of the Prior Art

U.S. Pat. No. 6,669,753, assigned to the Government of the United States of America, teaches that a small-scale reactivity test (i.e. SSRT) can measure the shock reactivity of explosive materials. The SSRT, as originally configured, consisted of four detonators in four separate holes in a steel confinement apparatus bonded to an aluminum dent block. In the example, ammonium nitrate formulations that have various levels of shock resistance are placed in the steel holes between the detonator and the aluminum dent block. Explosive performance is gauged by measuring the dent depth produced in the aluminum dent block.

While the related art test is useful for determining the prompt shock reaction of various explosive materials, it fails to quantify the total energy available to internal blast that also includes delayed shock reaction and combustion of remaining reactants with the air. The selection of the detonator can influence the results of the test. That is some detonators are encapsulated in polymeric materials that can burn, while in other detonators the detonating materials are encapsulated in non-organic materials that have a lower level of heat contribution. The contribution of the detonator is particularly important when evaluating the total output of a small scale explosive event, because unlike a large scale test where the contribution of the detonator is relatively small, the detonator material in a small test can account for a significant portion of the total explosive material. For example, in a large-scale test the explosive material weighs 23 Kg, whereas in an SSRT the explosive material is under 0.5 grams. In both tests, the detonator, such as RP-80, has 80 mg of PETN and 123 mg of RDX. In the large-scale test the detonator explosives would account for only ~9×10$^{-5}$% of the total, but in the small scale test the detonator explosives account for 40% or more.

Although related conventional art discusses a small scale reactivity test using conventional technology based on detonators containing polymeric materials, a small scale reactivity test is needed that measures not only shock sensitivity and reactivity, but also any ancillary reactions that occur in addition to the shock reaction, where the tests takes into account factors that are an artifact of the small scale of the test. Furthermore, while the SSRT measures the substantially instantaneous reaction, it does not measure the internal blast reaction, that is the total reaction. Unburned materials and gases given off by the initial reaction create a second slower burning reaction using the ambient oxygen, and this second reaction contributes to the internal blast reaction. The sum of the shock reactivity reaction (the fast reaction) and the post reaction (which is substantially a slower reaction) constitutes the total reaction. (e.g., the internal blast reaction). Further, a test is needed to resolve the total reaction into its component reactions.

SUMMARY OF THE INVENTION

The inventors have devised an apparatus and a method for studying the internal blast. High confinement allows the use of small samples, well below critical diameter, to model the results of large scale explosions. The effect of excess fuel, inside or outside the explosive, is clearly seen, and affects the correlation of quasi-static pressure with heat of combustion. The invention is the apparatus and the method for conducting a small-scale shock reactivity reaction and internal blast reaction test (SSBT). The apparatus includes a small scale shock reactivity test (SSRT) device, and an internal blast test device including: a pressure chamber that has an accessible interior, a pressure transducer having an output that is proportional to a pressure in the interior, a multipurpose port that provides an electrical connection to the shock reactivity test device, and a small gas port for flushing with a purge gas. The small scale shock reactivity test device is housed within the pressure chamber, and gases and materials produced during a small scale shock reactivity test are quasi-statically retained by the pressure chamber. The pressure transducer is in electrical communication with an instrument that can display the pressure detected in the pressure chamber. In an exemplary embodiment, the pressure transducer is a piezo-resistive transducer having a response time on the order of a few microseconds, a pressure detection range up to 200 psi over a compensated temperature range of 25 to 232° C. An instrument suitable for displaying the signal received from the transducer is a digital oscilloscope sampling at a rate that is at least twice per millisecond, and, in an exemplary embodiment, 50 times per millisecond.

The method for small-scale shock reactivity and internal blast test includes the steps of: initiating a small scale reactivity test device for producing an initial reaction by a detonator and an internal blast reaction produced by subsequent detonation of the test sample; measuring the contribution of the detonator, in an air filled pressure chamber, to the small-scale shock reactivity and internal blast test (SSBT) as indicated by a rise in a peak quasi-static pressure ($D_A$) following initiation of the detonator; measuring the contribution of the detonator, in an inert gas filled pressure chamber, to the SSBT as indicated by a rise in the peak quasi-static pressure ($D_N$) following initiation of the detonator; measuring the combined contribution of the detonator and a test explosive, in an air filled pressure chamber, to the SSBT as indicated by a rise in a peak quasi-static pressure ($E_A$) following initiation of the detonator; measuring the combined contribution of the detonator and a test explosive, in an inert gas filled pressure chamber, to the SSBT as indicated by a rise in a peak quasi-static pressure ($E_N$) following initiation of the detonator; and analyzing the results.

The pressure measurements are analyzed as to the shock reaction and addition of delayed reactions to the internal blast explosion. The increase in pressure that can be attributed to the shock reactivity ($SR_D$) of the detonator is $D_N$; an increase in pressure that can be attributed to the slow burn reaction combustion of any remaining reactants in air ($SB_D$) of the detonator is ($D_A-D_N$); an increase in pressure that can be attributed to the shock reactivity ($SR_E$) of the test explosive is ($E_N-D_N$); a total increase/internal blast ($IB_E$) in pressure that can be attributed to the test explosive is ($E_A-D_A$); and an increase in pressure that can be attributed to the slow burn reaction combustion ($SB_E$) of any remaining reactants in air of the test explosive is $(E_A-D_A)-(E_N-D_N)$, where $IB_E=SR_E+SB_E$. The analysis quantifies the increase in internal blast explosion that occurs when ambient oxygen and unburned materials are present in the pressure chamber. If there is no oxygen present (only inert nitrogen), then there is substantially no secondary reaction, as substantially few of the slow burn reactants combust following the shock reactivity explosion, and $SB_E=SB_N=0$.

BRIEF DESCRIPTION OF THE DRAWINGS

The foregoing invention will become readily apparent by referring to the following detailed description and the appended drawings in which.

DETAILED DESCRIPTION

Figure 1:
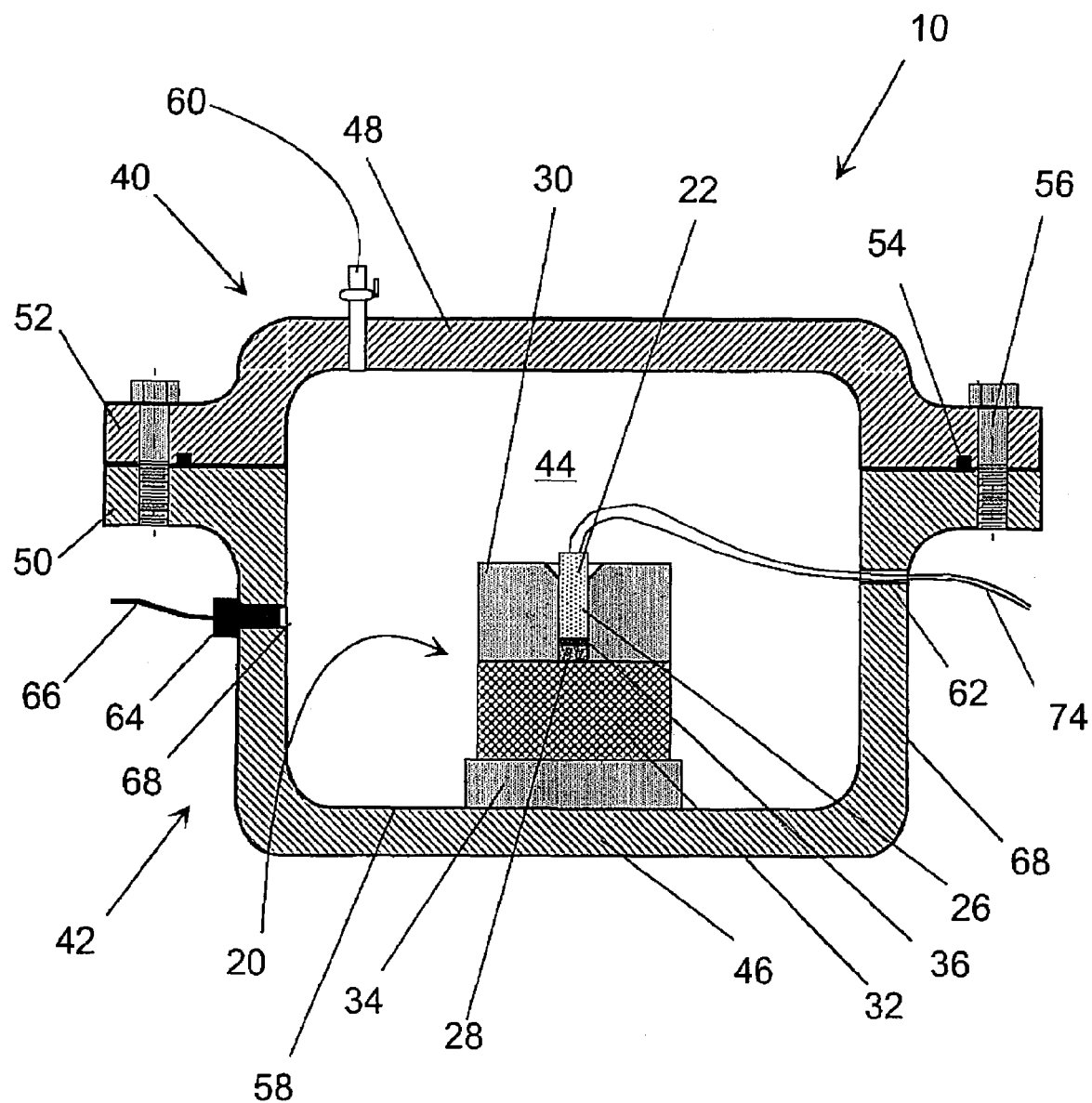
FIG. 1 is a cross-sectional view of an exemplary embodiment of an apparatus for conducting a small-scale shock reactivity and internal blast test (SSBT) illustrating a small scale shock reactivity test (SSRT) device and internal blast test device.

The invention is the apparatus and the method for conducting a small-scale shock reactivity reaction and internal blast reaction test (SSBT). The apparatus is illustrated in FIG. 1. The apparatus 10 includes a small-scale shock reactivity test (SSRT) device 20, and an internal blast test device 40. The internal blast test device 40 includes a pressure chamber 42 with an accessible interior 44. The pressure chamber is generally a cast aluminum rectangular chamber 42 that, in an exemplary embodiment, has a volume of about 3 liters. The chamber includes a flanged vessel 46 and a covering flanged top 48. The flanged vessel 46 and the flanged top 48 are sealed with at least one gasket type O-ring 54 and multiple bolts 56 that connect the top flange 52 to the vessel flange 50. A wall 68 of the vessel has a transducer port 68 that enables a pressure transducer 64 to measure the pressure in the interior 44 of the pressure vessel. In an exemplary embodiment, the transducer is a piezo-resistive transducer having a response time on the order of a few microseconds, with a pressure detection range up to 200 psi over a compensated temperature range of 25 to 232° C. The Kulite® XTE-190 transducer is a suitable transducer, having an excellent response time and a rugged construction. Lead 66 carries the signal from the transducer 64 to an instrument (not shown) suitable for displaying the signal. A digital oscilloscope sampling at a rate that is at least twice per millisecond, and, in particular, 50 times per millisecond is a suitable instrument. An example of the display instrument is a Nicolet® Integra 40 oscilloscope. The pressure chamber 42 has a small gas port 60 for flushing the chamber with a purge gas. The purge gas is usually employed when it is desired to conduct the test with a substantially inert gas. The inert gas is selected from the group consisting of nitrogen, helium, neon and argon. Nitrogen is usually sufficiently inert, and is relatively inexpensive as compared to the Nobel gases. The small gas port 60 can optionally be sealed, for instance with a valve, or be left open. The pressure chamber also has a multipurpose port 62 that provides an electrical connection via leads 74 to the shock reactivity test device 20.

The multipurpose port 62, in addition to providing a passage for the leads 74 to the detonator 22, also serves as an outlet port when purge gases are employed, and produces a quasi-static pressure in the chamber 42 during the SSBT test, because the gases in the chamber are heated by the SSRT test, and gases formed by the explosion contribute to the total moles of gases contained in the chamber. For a brief period of time, following ignition, the conditions inside the chamber are essentially static, as there is not sufficient time to significantly drain down the pressure. Hence the pressure in the chamber is "quasi-static" because the chamber is sealed except for the multipurpose port. Pressure decays as the product gases cool and slowly vent through the multipurpose port 62. In the SSBT, the pressure decays by 80-90% in 0.5 s.

Figure 2:
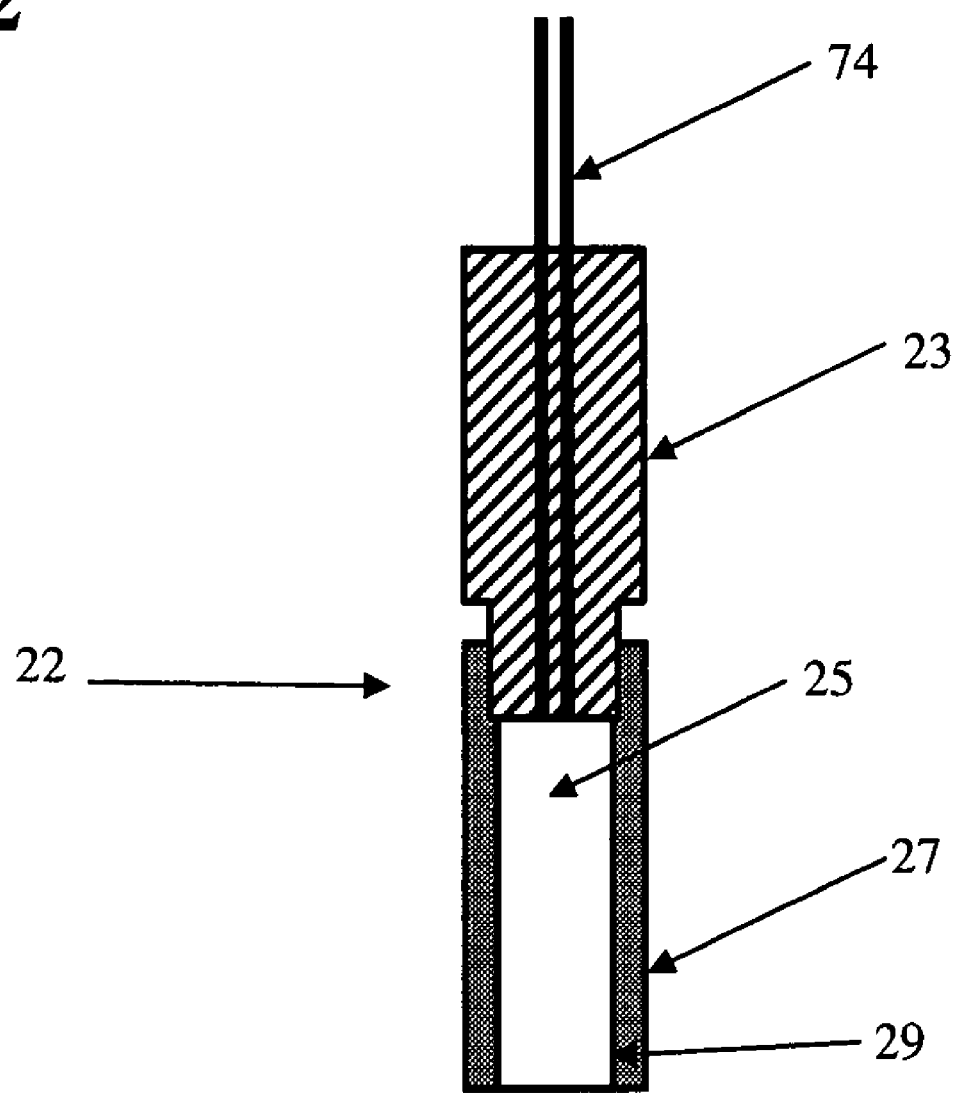
FIG. 2 is a cross sectional view of an exemplary embodiment of a detonator.

The SSRT device 20 in the illustrated embodiment is positioned on the floor 58 of the pressure chamber 42. The SSRT device 20 includes, in an exemplary embodiment, a steel containment block 30 with a center bore cavity 26; an aluminum alloy witness block 32 having an upper surface that is flush adhered to a bottom surface of the steel containment block 30; an electrically actuated detonator 22 mounted in the center bore cavity 26; and a test cavity 28 located in the center bore cavity 26 between the witness block 32 and the detonator 22. In an alternate exemplary embodiment, the test cavity 28, which may contain a test explosive material, is located in the center bore cavity between the witness block 32 and a gap or "space" 36, where the gap 36 is situated intermediate the test cavity 28 and the detonator 22. In an exemplary embodiment, a detonator 22 is illustrated in FIG. 2. The detonator includes leads 74 extending into a header 23 where the header 23 extends into a sleeve 27. The sleeve 27 forms a cavity 29 containing a portion of the header 23, and also contains an explosive material 25, such as, for example, PETN. The header 23 may be situated above the explosive 25 so the leads 74, which extend through the header 23, may initiate the explosive material 25 to produce an initial reaction. Upon subsequent ignition of the explosive material 25, test material (not shown) in the test cavity 28 may ignite and burn, which produces the internal blast reaction, that is, the desired output of the test.

In an exemplary embodiment, the detonator 22 is a special bare version of the Teledyne® RISI RP-80 detonator having a sleeve 27 that is available in Delrin®, a polyoxymethylene polymer manufactured by Dupont, or available in brass. In an exemplary embodiment, the sleeve 27 may be brass as it contributes less to the quasi-static pressure produced by the detonator alone. In an exemplary embodiment, the header 23 may be made from glass. An unexpected result is that the header 23 made from glass provided superior performance by increasing the accuracy of the inventive small-scale shock reactivity and internal blast test compared to conventional headers composed of glass and plastic or polymeric material, for example, glass fiber filled plastic headers. In particular, the header 23 made from the glass contains no fuel material, that is, no plastic or polymeric material, and generates a very minimal energy output during the initial reaction, and more particularly, about zero (Joules) energy output when burned, that is, initiated, during the initial reaction or detonation. Accordingly, the explosive 25 contributes the majority of the energy output (Joules) during the initial reaction, whereas the header 23 contributes about zero (Joules) energy output during the initial reaction.

In contrast, in the conventional glass fiber filled plastic header, the plastic component is a fuel material, which generates energy (Joules) when burned. The presence of the plastic component about doubles the energy output when the conventional header with plastic is burned compared to the header 23 made from glass without a plastic or polymeric component. In an exemplary embodiment, the inventive test using a header 23 made from glass material, as indicated below, results in a more accurate measurement of the test explosive material. As indicated, a conventional glass filled plastic header produces significant energy independent of the energy generated from the test explosive material thus overwhelming the test process with its energy output.

Accordingly, the large energy output from the glass filled plastic header significantly masks and skews the results by decreasing the ability to measure, accurately, the actual energy output, and other related test parameters, of the test explosive material located in the test cavity 28.

"Burned" means being exposed to a high temperature and pressure of an explosive charge as well oxygen from air and the detonation product gases.

The aluminum alloy witness block, in an exemplary embodiment, is a 6063 aluminum alloy having a T5 temper. This alloy is a relatively soft aluminum. In the illustrated embodiment, the SSRT device is seated on a Lexan pad, where Lexan® is a polycarbonate polymer manufactured by General Electric.

Example 1 (Actual)

The pressure chamber 42 was cast aluminum with internal dimensions 15×15×12.5 cm, with 1.3 cm wall thickness (AXJ664-N4, made by Akron Electric, Inc.), and scaled closely to a large-scale chamber. The rectangular geometry was presumed to give good air-mixing. The chamber was sealed except for a 3 mm multipurpose port 62 for detonator leads 74 and a small gas port 60 for flushing. A pressure transducer 64 was centrally mounted in one chamber wall 68. The SSRT device 20 included a steel block 30 that is 51×51×25 mm high. The center bore 68 had a diameter of 7.24 mm. The witness block 32 was 51×51×25 mm high, and adhered to the steel block with a thermoset adhesive. Leads 74, which were Teflon® coated, entered and were attached to the detonator 22, which was made of glass without plastic. The chamber pressure was measured with a Kulite XTE-190 piezo-resistive transducer having a response time of a few microseconds. The transducer was powered by a 9V battery and recorded without amplification on a Nicolet Integra 40 oscilloscope, with a 5 ms pre-trigger in all tests.

SSBT Test 1 (Actual Test)

Figure 3:
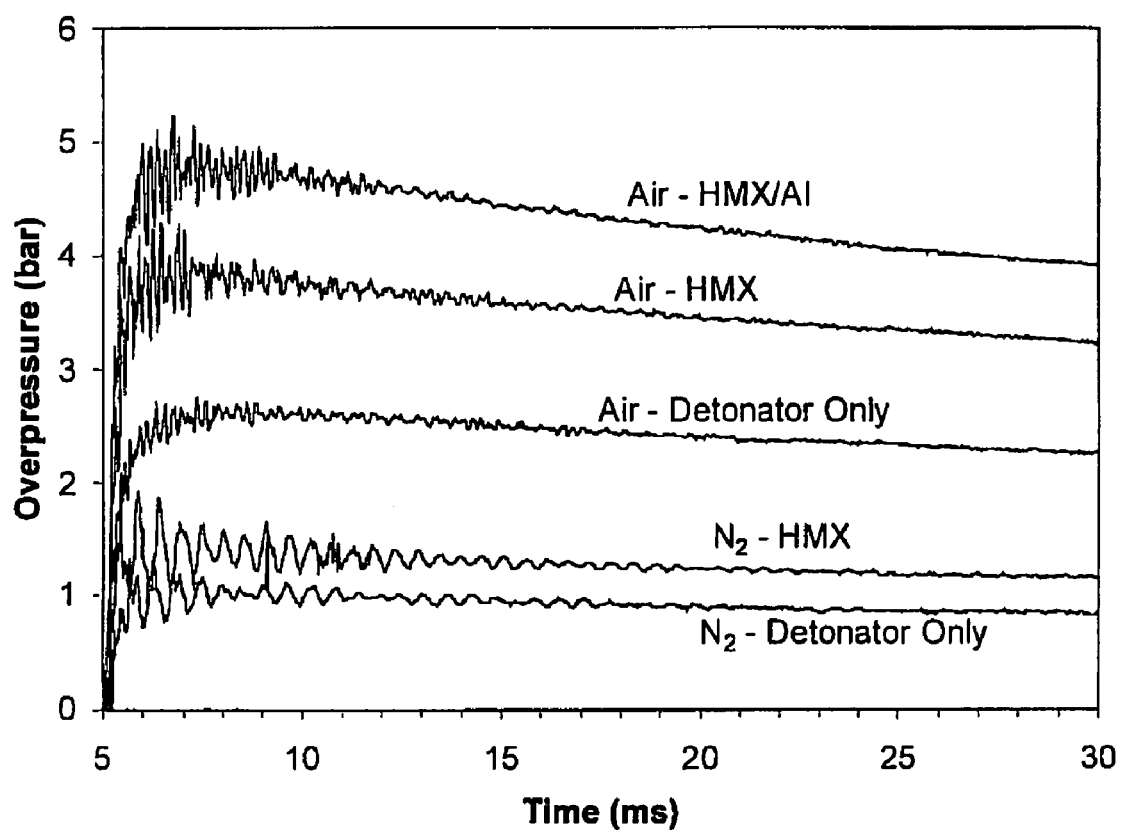
FIG. 3 is a graph of the results of small-scale shock reactivity and internal blast test (SSBT) illustrating the effect of the presence of air versus nitrogen in the pressure chamber, and the contribution of the detonator toward the quasi-static pressure that is attained when the test is conducted.

The graph shown in FIG. 3 illustrates the contribution of the detonator and the significant effect of the type of atmosphere on the quasi-static pressure attained in the test. The SSBT test was run with no sample in pressure chamber filled with nitrogen ($D_N$) and filled with air ($D_A$). The detonator 22 has 0.204 g of pentaerythritol tetranitrate (PETN), and from inspection, in the absence of air the quasi-static pressure ($D_N$) was about 1.0 bar after 10 ms. In the presence of air, the quasi-static pressure ($D_A$) was about 2.9 bar after 10 ms. When the test cavity was filled with 0.3 g of HMX Class 1 powder, the quasi-static pressure ($E_N$) was about 1.4 bar after 10 ms., not much higher than the detonator alone ($D_N$). In air, the 0.3 g of HMX Class 1 powder produced a quasi-static pressure ($E_A$) of about 6.3 bar after 10 ms. The increase in pressure that can be attributed to the shock reactivity explosion $SR_D$ of the detonator is 1.0 bar ($D_N$). The increase in pressure that can be attributed to the slow burn reaction $SB_D$ of the detonator is 1.75 bar ($D_A$–$D_N$), for a total internal blast of the detonator contribution of 2.75 bar ($D_A$).

The total increase in pressure that can be attributed to the internal blast of the test explosive was $IB_E$, where $IB_E$ included a shock reaction component $SR_E$ and a slow burn reaction component $SB_E$, or alternatively stated $IB_E$ was ($E_A$–$D_A$), where $D_A$ was the contribution by the detonator made of glass without plastic. The total increase in pressure attributed to the 0.3 g of HMX explosive then was 3.55 bar (6.3–2.75). The increase in pressure attributed to the shock reactivity explosion $SR_E$ of the test explosive was 0.3 bar, ($E_N$–$D_N$) or (1.3–1). The slow burn component $SB_E$ then was $IB_E$–$SR_E$, which was 3.25 bar (3.55–0.3). The SSBT can resolve the explosion into each of the reaction mechanisms, and accommodate for the effect of the detonator.

A fifth line on the graph was a test explosive mixture of 0.3 g of HMX and 0.075 g of finely ground aluminum (8 microns). A 20% addition of aluminum resulted in an increase in pressure to 7 bar, 10 ms after detonation. After subtracting out the contribution of the detonator, there was a total pressure increase attributed to the test explosive ($IB_E$) of 4.25 bar (7–2.75). 4.25 bar was a 20% increase over 3.55, illustrating the linearity of the test method.

As can be seen from the graph in FIG. 3, the shock wave, produced by the detonation of the test explosive and the detonator (without plastic) itself, reverberates inside of the pressure chamber, essentially producing a ringing. The ringing was evidenced by the vibration of the quasi-static pressure decaying in a matter of 10-20 ms.

The method for conducting a small-scale shock reactivity and internal blast test included the steps of: measuring the contribution of the detonator, in an air filled pressure chamber, to the small-scale shock reactivity and internal blast test (SSBT) as indicated by a rise in a peak quasi-static pressure ($D_A$) following ignition of the detonator; measuring the contribution of the detonator, in an inert gas filled pressure chamber, to the SSBT as indicated by a rise in the peak quasi-static pressure ($D_N$) following ignition of the detonator; measuring the combined contribution of the detonator and a test explosive, in an air filled pressure chamber, to the SSBT as indicated by a rise in a peak quasi-static pressure ($E_A$) following ignition of the detonator; measuring the combined contribution of the detonator and a test explosive, in an inert gas filled pressure chamber, to the SSBT as indicated by a rise in a peak quasi-static pressure ($E_N$) following ignition of the detonator; and analyzing pressure measurements as to the shock reactivity explosion and the slow burn reaction. The increase in pressure attributed to the shock reactivity explosion ($SR_D$) of the detonator was $D_N$; an increase in pressure attributed to the slow burn reaction ($SB_D$) of the detonator was ($D_A$–$D_N$); an increase in pressure attributed to the shock reactivity explosion ($SR_E$) of the test explosive was ($E_N$–$D_N$); a total increase ($IB_E$) in pressure attributed to the explosion of the test explosive was ($E_A$–$D_A$); and an increase in pressure attributed to the slow burn reaction ($SB_E$) of the test explosive was ($E_A$–$D_A$)–($E_N$–$D_N$), where $IB_E$=$SR_E$+$SB_E$. The slow burn reaction occurs when ambient oxygen and unburned materials are present in the pressure chamber.

It is to be understood that the foregoing description and specific embodiments are merely illustrative of the best mode of the invention and the principles thereof, and that various modifications and additions may be made to the invention by those skilled in the art, without departing from the spirit and scope of this invention, which is therefore understood to be limited only by the scope of the appended claims.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What we claim is:

1. A method for conducting a small-scale shock reactivity and internal blast test, comprising:

initiating a small scale reactivity test device for producing an initial reaction and an internal blast reaction;

measuring a contribution of a detonator in an air filled pressure chamber to the small-scale shock reactivity and internal blast test (SSBT) as indicated by a rise in a peak quasi-static pressure ($D_A$) following ignition of the detonator;

measuring the contribution of the detonator in an inert gas filled pressure chamber to the SSBT as indicated by a rise in the peak quasi-static pressure ($D_N$) following ignition of the detonator;

measuring the combined contribution of the detonator and a test explosive, in an air filled pressure chamber, to the SSBT as indicated by a rise in a peak quasi-static pressure ($E_A$) following ignition of the detonator;

measuring the combined contribution of the detonator and a test explosive, in an inert gas filled pressure chamber, to the SSBT as indicated by a rise in a peak quasi-static pressure ($E_N$) following ignition of the detonator; and analyzing pressure measurements as to the shock reactivity explosion and the slow burn reaction.

2. The method according to claim 1, wherein an increase in pressure attributed to the shock reactivity explosion ($SR_D$) of the detonator is denoted by $D_N$; an increase in pressure attributed to the slow burn reaction ($SB_D$) of the detonator is denoted by ($D_A-D_N$); an increase in pressure attributed to the shock reactivity explosion ($SR_E$) of the test explosive is denoted by ($E_N-D_N$); a total increased pressure ($IB_E$) attributed to the explosion of the test explosive is denoted by ($E_A-D_A$); and an increase in pressure attributed to the slow burn reaction ($SB_E$) of the test explosive is denoted by ($E_A-D_A$)−($E_N-D_N$), where $IB_E=SR_E+SB_E$.

3. The method according to claim 1, further comprising causing an internal blast explosion by providing ambient oxygen and unburned materials in the air filled pressure chamber.

* * * * *